United States Patent
Brogan et al.

(10) Patent No.: US 10,548,637 B2
(45) Date of Patent: Feb. 4, 2020

(54) IMPLANTABLE BONE SUPPORT SYSTEMS

(71) Applicant: Osteosymbionics, LLC, Cleveland, OH (US)

(72) Inventors: Cynthia M. Brogan, Cleveland Hts., OH (US); Carl Michael Nilsson, Moreland Hills, OH (US)

(73) Assignee: BLOCKHEAD OF CHICAGO, LLC, Chicago, IL (US)

( * ) Notice: Subject to any disclaimer, the term of this patent is extended or adjusted under 35 U.S.C. 154(b) by 66 days.

(21) Appl. No.: 13/573,756

(22) Filed: Oct. 3, 2012

(65) Prior Publication Data

US 2013/0282011 A1 Oct. 24, 2013

Related U.S. Application Data

(60) Provisional application No. 61/624,281, filed on Apr. 14, 2012, provisional application No. 61/542,386, filed on Oct. 3, 2011.

(51) Int. Cl.
*A61B 17/68* (2006.01)
*A61B 17/88* (2006.01)
*A61B 90/00* (2016.01)

(52) U.S. Cl.
CPC ........ *A61B 17/688* (2013.01); *A61B 17/8869* (2013.01); *A61B 17/8872* (2013.01); *A61B 17/8863* (2013.01); *A61B 2090/037* (2016.02)

(58) Field of Classification Search
CPC .................................... A61B 17/688
USPC ........................................ 606/75
See application file for complete search history.

(56) References Cited

U.S. PATENT DOCUMENTS

| | | | |
|---|---|---|---|
| 2,576,649 A * | 11/1951 | Slind | 27/21.1 |
| D245,788 S | 9/1977 | Branch et al. | |
| 5,707,373 A | 1/1998 | Sevrain et al. | |
| 5,800,436 A | 9/1998 | Lerch | |
| 5,868,746 A | 1/1999 | Sarver et al. | |
| 6,022,351 A | 2/2000 | Bremer et al. | |
| 6,190,389 B1 * | 2/2001 | Wellisz | A61B 17/688 606/281 |
| RE37,249 E | 6/2001 | Leibinger et al. | |
| 6,258,091 B1 | 7/2001 | Sevrain et al. | |

(Continued)

FOREIGN PATENT DOCUMENTS

JP 2000139938 A * 5/2000 ........... A61B 17/688

*Primary Examiner* — Nicholas W Woodall

(57) ABSTRACT

An implantable bone support system including a shelf clip supported on a portion of the perimeter of the skull opening. The shelf clip includes upper and lower body portions. The legs of the lower body portion are positioned such that one leg is engaged with the skull perimeter in a direction away from the skull opening. The opposing leg is positioned into the skull opening to form a portion of a shelf for receiving the bone flap or implant. In an adjustable height embodiment, the ratcheting leg of the upper body portion engages a central post, via ratchet teeth on the leg and the central post, and is pressed into engagement to capture the skull between the upper and lower body portions. The removable or locking leg is formed for engagement with the upper body portion of the clip, and engages an external surface of the bone flap or implant to capture the bone flap or implant within the shelf created by the clips within the skull opening.

8 Claims, 11 Drawing Sheets

(56) References Cited

U.S. PATENT DOCUMENTS

| | | | |
|---|---|---|---|
| 6,379,363 B1* | 4/2002 | Herrington | A61B 17/688 606/104 |
| 6,485,493 B1* | 11/2002 | Bremer | 606/70 |
| 6,589,244 B1 | 7/2003 | Sevrain et al. | |
| 6,921,401 B2 | 7/2005 | Lerch et al. | |
| 7,048,737 B2 | 5/2006 | Wellisz | |
| 7,060,067 B2* | 6/2006 | Needham et al. | 606/86 B |
| 7,238,188 B2 | 7/2007 | Nesper et al. | |
| 7,361,178 B2 | 4/2008 | Hearn et al. | |
| 7,670,361 B2 | 3/2010 | Nesper et al. | |
| 7,993,349 B2 | 8/2011 | Hearn et al. | |
| 8,048,130 B2 | 11/2011 | Nesper et al. | |
| 8,226,694 B2 | 7/2012 | Broaddus et al. | |
| 2002/0016593 A1* | 2/2002 | Hearn | A61B 17/688 606/916 |
| 2002/0095156 A1* | 7/2002 | Kuras et al. | 606/72 |
| 2005/0107813 A1* | 5/2005 | Gilete Garcia | A61B 17/688 606/151 |
| 2005/0137608 A1* | 6/2005 | Hearn | A61B 17/688 606/103 |
| 2007/0100344 A1* | 5/2007 | Agbodoe | 606/69 |
| 2008/0051792 A1 | 2/2008 | Garcia | |
| 2008/0172097 A1* | 7/2008 | Lerch | A61B 17/688 606/324 |
| 2008/0249532 A1* | 10/2008 | Schoutens et al. | 606/99 |
| 2008/0281339 A1* | 11/2008 | Kirschman | A61B 17/688 606/151 |
| 2011/0022098 A1 | 1/2011 | Garcia | |

\* cited by examiner

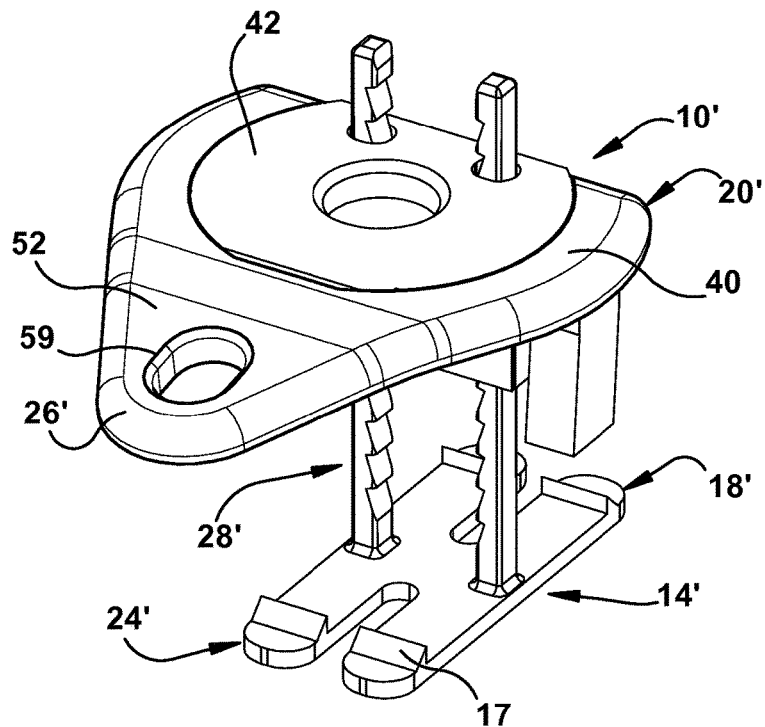
Figure 8
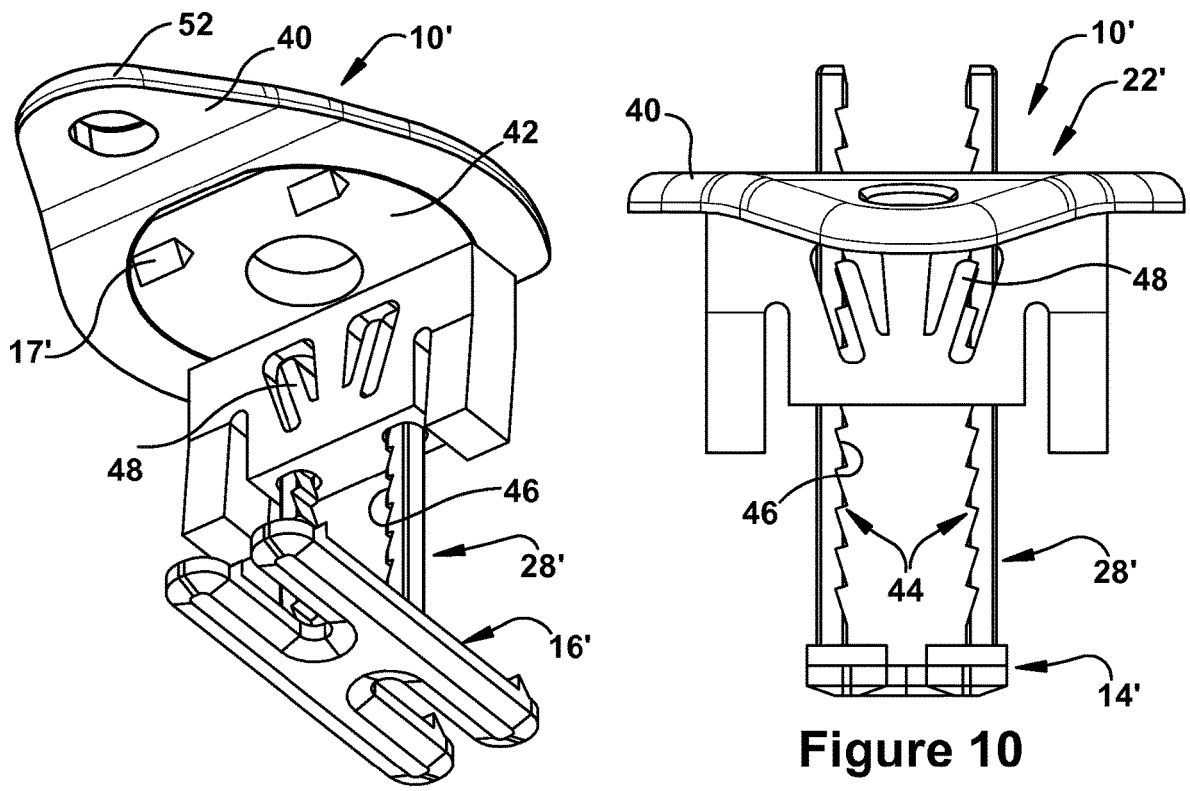
Figure 9
Figure 10

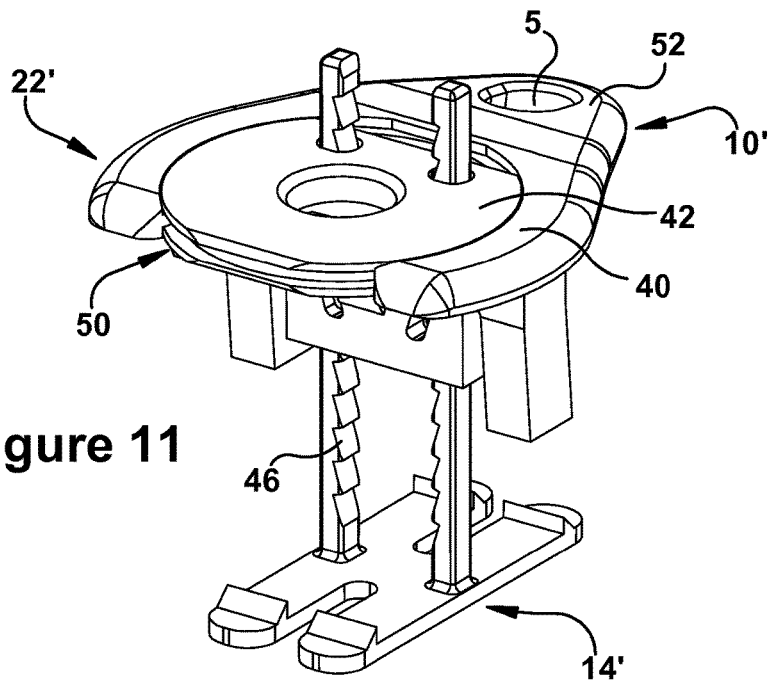
Figure 11
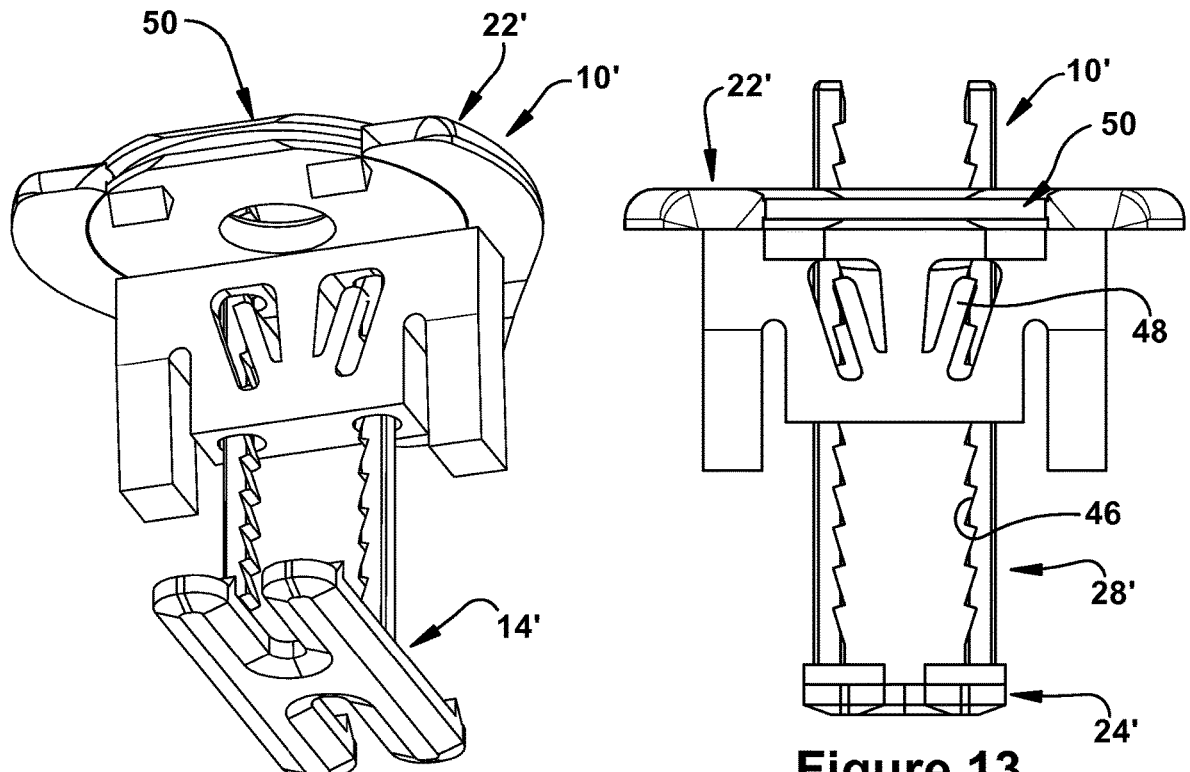
Figure 12
Figure 13

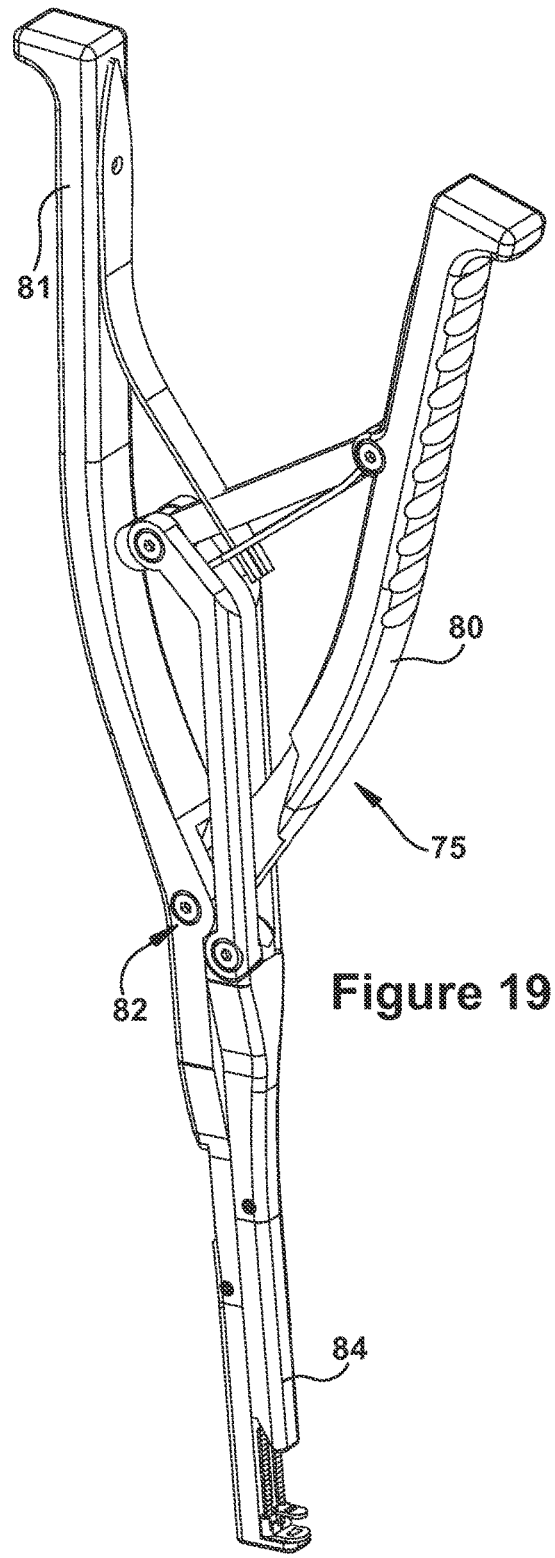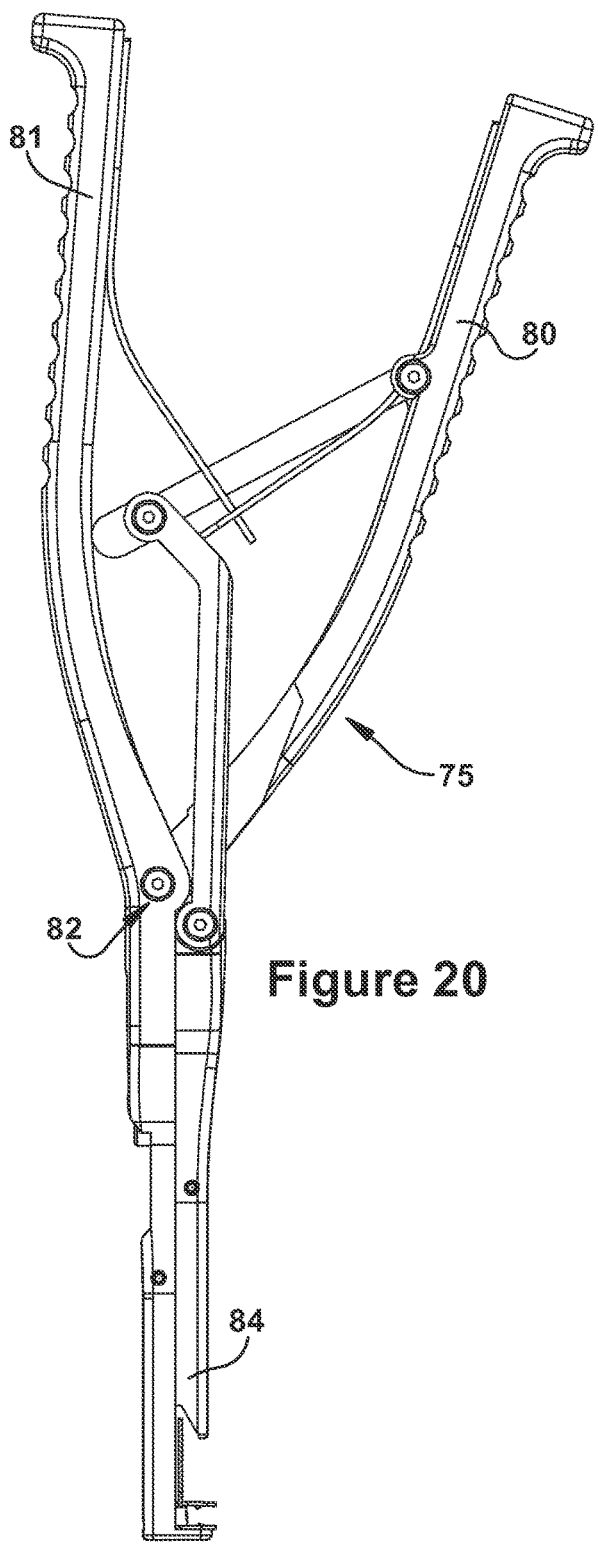

IMPLANTABLE BONE SUPPORT SYSTEMS

PRIORITY CLAIM

This application claims priority from provisional patent applications, Ser. Nos. 61/624,281 filed Apr. 14, 2012 and 61/542,386 filed Oct. 3, 2011, the subject matters of which are incorporated herein by reference in their entirety.

TECHNICAL FIELD

The present application is for an implantable bone support system, and more specifically for implanted devices or clips for stabilizing and supporting bone segments or custom-shaped implants within a skull opening.

BACKGROUND

A craniotomy is a surgical operation in which a bone flap is removed from the skull to access the brain. Craniotomies are often a critical operation performed on patients suffering from brain lesions or traumatic brain injury. Such surgical procedures are also conducted to allow doctors to surgically implant deep brain stimulators for the treatment of Parkinson's disease, epilepsy and cerebellar tremor. The location and amount of skull that needs to be removed depends to a large extent on the type of surgery being performed. In a craniotomy, the bone is replaced after access to the brain is completed.

To remove the bone flap, one common surgical practice is to drill 3 holes in a triangular pattern, and saw between the holes to form a triangular bone flap which is then removed to access the brain cavity. Alternatively, 4 holes may be drilled with the saw cuts forming a rectangle. More holes are possible depending on anatomy and the surgeon.

Following the performance of the necessary medical procedures, the bone flap must be replaced within the skull opening. Due to the use of a cutting tool the bone flap will be slightly smaller than the skull opening. A gap, formed between the skull opening and bone flap due to the kerf of the bone cutting instrument, is typically between 1 and up to 3 mm. In the past, fixation of the bone flap to the skull has been accomplished using a variety of methods and devices, but commonly, plates and bone screws are used to bridge and stabilize, respectively, the spaced apart bone segments. To secure the plates to each bone surface, at least 2 screws are used on each side of each plate (depending on plate geometry it can be either 1 or 2 screws, though 2 screws is more customary). Since the preferred technique uses 3 plates to fully stabilize the bone segments and ensure a strong attachment, this results in the use of up to twelve screws. The use of such a large number of screws requires the time consuming process of placing the screw includes potentially pre-drilling and tapping the holes and then inserting the screws, all conducted towards the end of the surgical procedure, thereby increasing the total surgery time.

Another bone flap replacement technique attempts to abut the bone flap against the skull opening to obtain a large surface of bone to bone contact in order to encourage bone growth across the two meeting bone segments, while securing the remaining portion of the perimeter opening with mortar and plates/screws. Such attempts have not been entirely successful, as the joint is brittle and the bone flap may not remain in position and that due to the kerf, the distance between the bone segments is now twice as big on the opposing side. In such applications, the bone flap is merely held in place, as the gap is not filled. Additionally, in the event it is desired that the bone screws and plates are flush with the skull, in order to avoid adhesions where the tissue and scalp contact the screws, further time consuming bone removal may be required. Still further, such attachment methods do not enable the ready removal of the screws to again remove the bone flap to reaccess the brain cavity in the event further surgery and surgical procedures are required. As a result, additional bone removal may be required to remove the bone screws in the event that cannot be unscrewed.

An additional prior art method for repositioning the bone flap which does fill the gap is a Cranial LOOP™ device manufactured by NEOS Surgery S.L. of Barcelona, Spain, as disclosed in U.S. Patent Application Pub. No. 2008/0051792. This type of device is positioned within the gap between the bone flap and skull and acts like a grommet to sandwich the bone flap, but does not support or carry the weight of the bone flap. Additional devices along these lines are also shown in U.S. Pat. No. 6,022,351 to Bremer and U.S. Pat. No. 6,379,363 to Herrington, for example.

SUMMARY

The present application provides an improved implantable bone support system which solves numerous problems. The present system may be used in connection with kerf or gap filling situations or no kerf trauma applications, as well as for placing PMMA, PEEK, titanium or ceramic implants. The bone support system includes a titanium shelf clip which may be attached alone or at numerous positions surrounding the perimeter of the opening formed in the skull. The shelf clips support the bone flap or implant within the skull opening and prevent it from entering the brain cavity. The use of at least 2-3 shelf clips forms an interior shelf for supporting and engaging the bone flap or implant which may then be further secured. While at least 3 shelf clips may be preferred to provide a fully supported interior shelf for the bone flap or implant, more clips may be used as needed for additional support.

The bone support system provides a simple, fast and easy method and device for supporting the bone flap or implant and eliminates the need for the time consuming use of screws. As a result, surgical time to install the bone support system is reduced. Additionally, the shelf clips have a smooth and low profile which avoid adhesions and engagement issues between the skull and the scalp tissue. Still further, the shelf clips may be readily removed in the event further surgery is required to remove the bone flap and re-access the brain cavity.

The shelf clip of the implantable bone support system includes a lower body portion having a base and opposing barbed legs extending from the base for engagement with the skull and with the bone flap. The base also supports a central post, supporting an upper engagement portion having a locking leg for engagement with the skull and a removable leg for engagement with the bone flap or implant. The leg which engages the bone flap or implant may be of a variety of sizes and shapes, but may also itself be large enough to serve as a cover over the skull opening. In one embodiment, the central post is provided as two posts having ratchet teeth for ratcheting engagement with the upper engagement portion. The clip components may be stamped metal members or injection molded parts, which may be formed of numerous well known long term biocompatible implant materials, such as stainless steel, titanium or PEEK.

The shelf clip is supported on a portion of the perimeter of the skull opening. The legs of the lower body portion are positioned such that one leg is engaged with the perimeter in a direction away from the skull opening. The opposing leg is positioned into the skull opening to form a portion of the shelf for receiving the bone flap. The locking leg of the upper body portion engages the central post, via ratchet teeth on the locking leg and the central post, and is pressed into engagement to capture the skull between the upper and lower body portions. The removable leg is formed for engagement with the upper body portion of the clip, and engages an external surface of the bone flap or implant to capture the bone flap or implant within the shelf created by the clips within the skull opening. The clips are held in place by retention barbs or holes formed in each leg, since each clip must be held in position on the skull without manual assistance, screws or suturing when the bone flap is placed within the skull opening.

BRIEF DESCRIPTION OF THE DRAWINGS

FIG. 8 is a front top perspective view of an alternate embodiment of a shelf clip of the present application, where the upper swivel portion of the clip is in the "closed" position for capturing the bone flap or implant;

FIG. 9 is a front bottom perspective view of the closed position shelf clip embodiment of FIG. 8;

FIG. 10 is a front view of the closed position shelf clip embodiment of FIG. 8;

FIG. 11 is a front top perspective view of the shelf clip embodiment of FIG. 8, where the upper swivel portion of the clip is in the "open" position for receiving the bone flap or implant within the skull opening;

FIG. 12 is a rear bottom perspective view of the open position shelf clip embodiment of FIG. 8;

FIG. 13 is a rear view of the open position shelf clip embodiment of FIG. 8;

FIG. 18b is a further enlarged schematic view of the shelf clip of FIG. 18a;

FIG. 19 is a perspective view of an insertion tool for ratcheting the locking or ratcheting leg;

FIG. 20 is a side view of the insertion tool of FIG. 19;

FIG. 23c is a front perspective view of the shelf clip of FIG. 23a.

DETAILED DESCRIPTION

Figure 1:
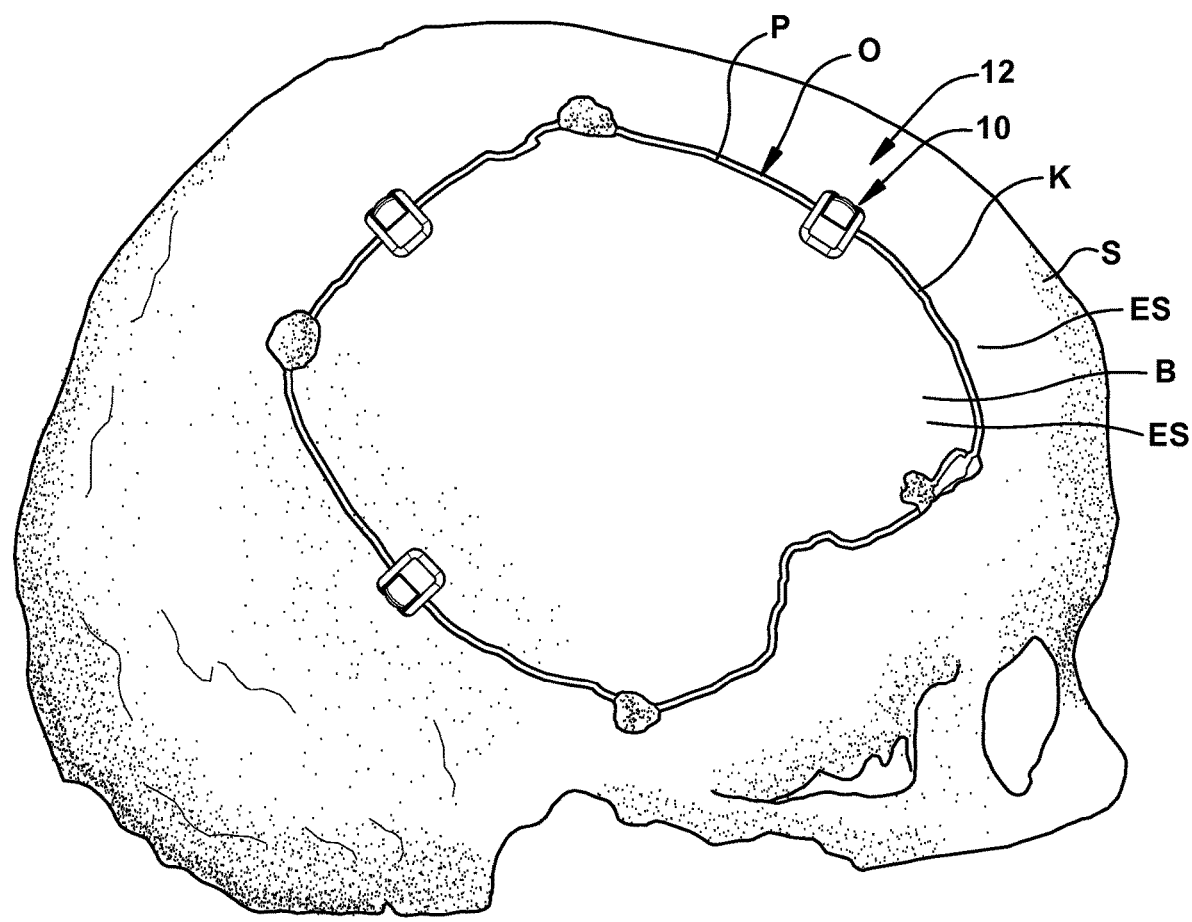
FIG. 1 illustrates a skull having multiple holes drilled to form a skull opening and remove a bone flap in order to access the brain cavity, and an implantable bone support system of the present application using clips to support the bone flap for replacement within the skull opening following surgery.
Figure 2:
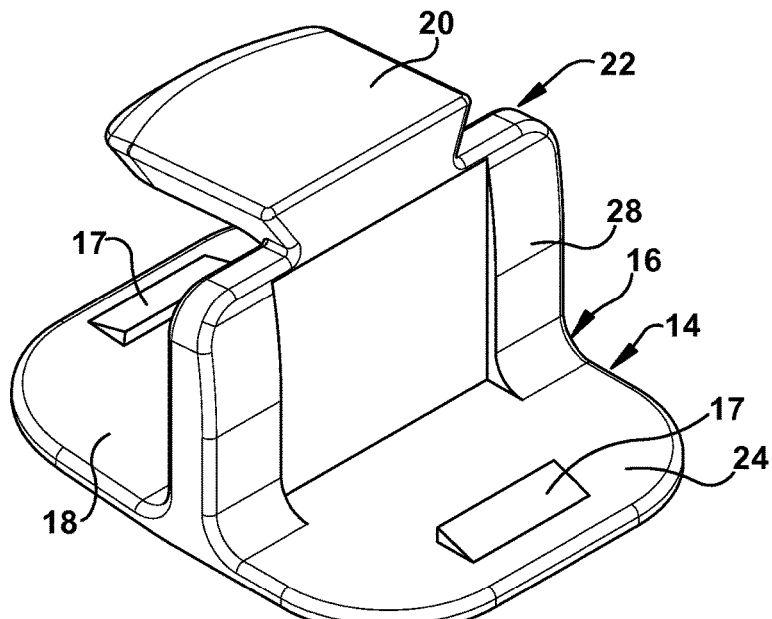
FIG. 2 is a perspective view of one part of a two-part shelf clip.
Figure 3:
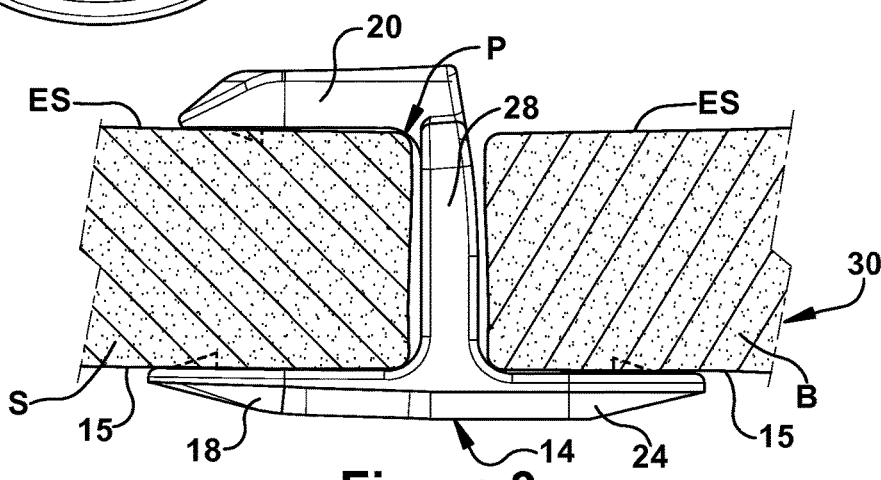
FIG. 3 is a schematic side view of the shelf clip of FIG. 2, and showing a cut-away skull captured by the shelf clip, and the bone flap supported on the clip.

The implantable bone support system 12 illustrated in use in FIG. 1 provides a simple, fast and easy device and method for supporting the bone flap or implant B that eliminates the need for the time consuming use of screws, so surgical time to install the bone support system is reduced. The shelf clips 10 of the present application have a smooth and low profile which avoid adhesions between the skull S and the scalp tissue T, and may be readily removed in the event further surgery is required to remove the bone flap B. In the descriptions of the embodiments which follow, where components have the same name, they may be referred to using the same reference character, or using the same reference character but with a prime designation.

In the illustrated embodiment of FIGS. 2 to 7, a two-part, fixed height shelf clip 10 is provided. The clip 10 includes a lower body portion 14 having a base 16 with opposing legs 18, 20 extending from the base, and also includes an upper body portion 22. A central post 28 extends between the lower and upper body portions 14, 22. The upper and lower body portions include 3 legs; 2 of which are spaced apart from one another by the fixed height base 16 and extend in a direction away from the base to engage the external ES and internal surfaces IS of the skull S, called the skull legs, 18, 20. The third leg, the bone flap support leg 24, extends in a direction opposite from the skull legs 18, 20, such that when the bone flap B is repositioned within the skull opening O on a shelf 30, it is supported on the bone flap support leg. The central post 28 is eventually located within the kerf gap K and can act as a compression wedge for additional support and stabilization and location.

The shelf clip 10 is supported surrounding a portion of the perimeter P of the skull opening O using the illustrated clip 10 having central post 28 and 3 legs, with a fourth leg formed by a locking cap 26 which is engaged with and secured to the clip 10 and engages an external surface ES of the bone flap B to capture the bone flap within or on shelf 30 created by the clips 10 upon repositioning of the bone flap B within the skull opening O to create the implantable bone support system. The clips 10 are held in place by retention barbs 17 illustrated as positioned on each leg, since each clip 10 must remain in position on the skull S without manual assistance, screws or suturing when the bone flap B is placed within the skull opening O during formation of the shelf 30.

Figure 4:
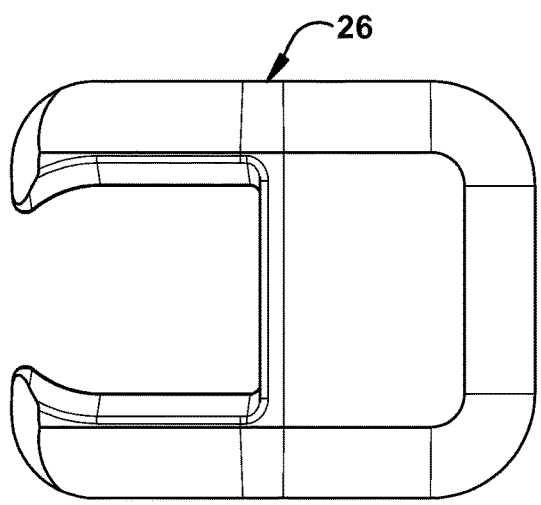
FIG. 4 is a top view of the second part or locking cap of the two-part shelf clip.
Figure 5:
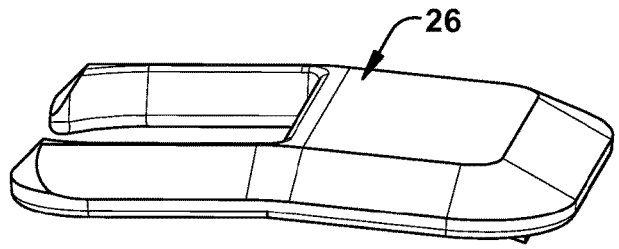
FIG. 5 is a perspective view of the locking cap of FIG. 4.
Figure 6:
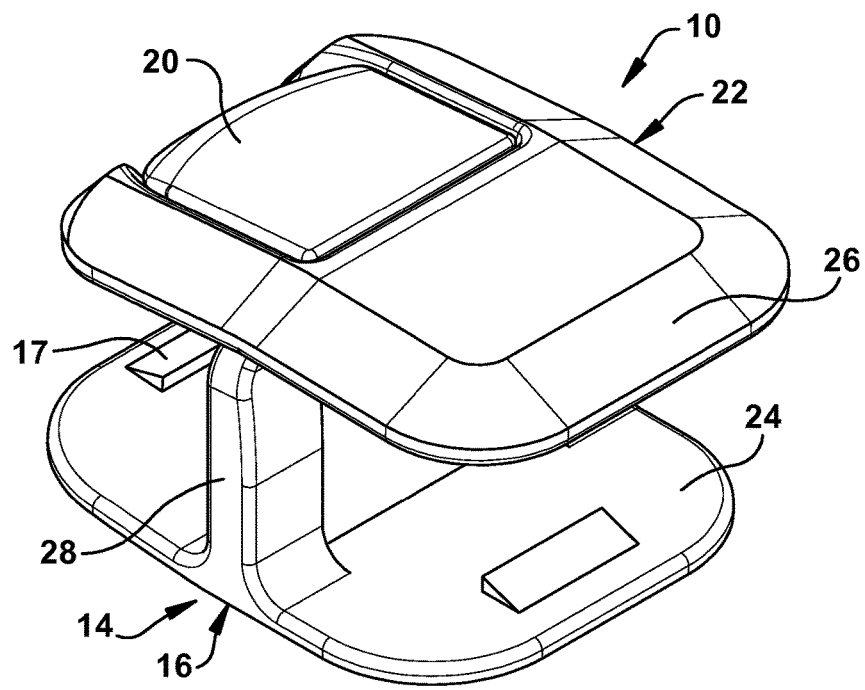
FIG. 6 is a perspective view showing the two parts of the two-part shelf clip engaged together.

The locking cap or leg 26 may be formed as a separate piece, as shown in FIGS. 4 and 5, or as a one piece clip, not illustrated, with a movable locking leg which pivots, flips on a hinge or slides. Once the bone flap B is positioned within the skull opening O the locking leg 26 is moved into locked or closed position to capture the bone flap. In the two-piece embodiment of FIGS. 2-7, the locking leg or cap 26 has a surface for mating engagement with the shelf clip 10, and slides into closed position under either a friction fit engagement or a defined positive engagement (e.g. a designed slot/hook engagement) once the bone flap B is positioned on the shelf 30. The central post 28 may be provided with a fixed or adjustable height, as in FIGS. 8-13, so that variances in bone skull S thickness (often ranging from 3 mm to 20 mm) may be readily accommodated. No special surgical instrumentation or other tools are required for installation of this clip embodiment.

In still another embodiment, shown in FIGS. 8 to 13, 3-4 of the shelf clips 10' of the illustrated invention are first placed on the skull S spaced around the perimeter P of the skull opening O, similar to the configuration shown in FIG. 1. The clip 10' enables temporary placement of a height or skull-thickness adjustable clip that creates a shelf-like feature to place and support the bone flap or implant B. In this 3 piece adjustable height clip 10' embodiment, a lower body portion 14' is provided. An upper body portion 22' is also included having an external rotating portion 40 and a central portion 42 for engagement with the central post 28' is provided. As shown, the lower body portion 14' includes opposing barbed legs 18' 24' extending from a base supporting two central posts 28', where each post contains a ratchet surface 44 or surfaces with angled teeth 46. In this embodiment, the opposing barbed legs of the lower body portion 14' form an H-shaped configuration. The teeth 46 of the central posts 28' are angled to enable locking engagement when angled ribs 48 on the central portion 42 are engaged over the angled teeth 46 of the central posts 28' to resist removal of the upper body portion 22' of the clip 10' from the lower body portion 14'. The ability to quickly and easily place and retain the clips in position on the perimeter P of the skull opening O as a first step in use of the device is unlike any prior art device or method currently used. Prior art devices typically require multiple holding devices to retain the fixation devices in position until the bone flap is inserted. No such inconvenient positioning and holding of multiple devices is provided with the present invention.

Following placement of the clips 10', pushing down the central portion 42 of the upper body portion 22' onto the central posts 28' enables height adjustment of each clip on the skull S. The bone flap or implant B is then inserted into the opening O in the skull S and supported on the legs 24' or shelf 30 extending from the lower body portion 14'.

In the embodiment of FIGS. 8-13, once the bone flap or implant B is inserted into the skull cavity opening O, the rotating portion 40 of the clip 10' is rotated, approximately 180 degrees, on the central portion 42 of the clip, engaged and supported within a rail or mating tongue and groove structure 50 provided between the central portion 42 and rotating portion 40 of the upper body portion of the clip. The rotating external portion 40 of the clip 10' includes a rounded and extending boss portion 52 which extends over the bone flap B to "sandwich" the bone flap between the bone flap support leg 24' of the clip and the rotated boss portion 52 of the clip, to thereby support and capture the bone flap B within the skull opening O. It is noted that an opening 54 is provided in the boss portion 52 of the clip 10' in the event additional fixation using conventional screws through the opening 54 is desired.

In a preferred form of this embodiment, the clip components are stamped metal members which may be formed of numerous well known and appropriate implantable metal materials, such as titanium or surgical stainless steel. Alternatively, the device may be from other appropriate prior art polymer materials such as PMMA or PEEK, or of resorbable materials also known to those of ordinary skill in the art. When used with resorbable material, the central portion of the upper body portion of the clip acts as a filler or a wedge within the kerf or gap K. When functioning as a wedge under the application of compression loads on the clip of the present bone support system 12, the resorbable material becomes especially important, since it carries the load and promotes bone growth across the kerf K. This is not the case with conventional screws and plates, since the kerf is not filled, and the plates hold the flap in a cantilever fashion. While prior art "sandwich" devices may have a portion of the device within the kerf, they are not designed to carry a compression load or to act to promote bone growth across the kerf.

Still further embodiments of the shelf clip 10", 10''', 10'''' are shown in the embodiments of FIGS. 16a to 18b, FIG. 14 and FIG. 15, respectively. The device includes several components supported on a lower body portion 14, and an upper body portion 22. The lower body portion formed on base 16 includes a skull leg 18" and a bone flap support leg 24". The upper body portion includes a ratcheting leg 20" and a locking leg 26". A central post 28", taking the form of two posts each having a ratchet surface 44" with ratchet teeth 46", interconnects the upper and lower body portions. The ratcheting leg 20" is formed integral with a sleeve 60 which surrounds the central post 28" and each of the ratchet surfaces 44". The sleeve 60 includes a mating tooth surface 62 which is positioned to engage the ratchet teeth 46" of the central post 28" and resist removal of the ratcheting leg 20" and sleeve from the central post as the ratcheting leg is pushed toward the lower body portion 14.

Figure 16A:
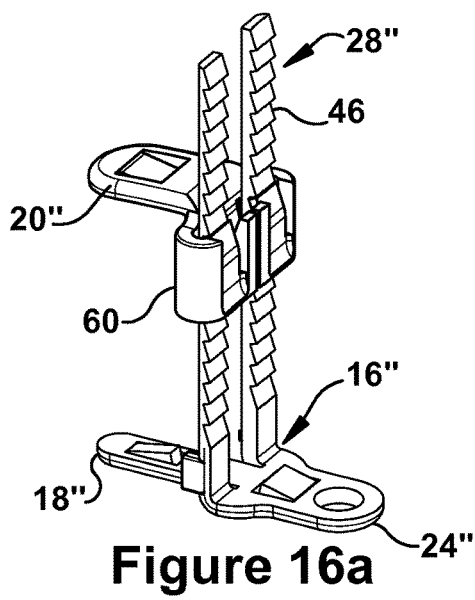
FIGS. 16a and 16b are perspective views of another alternate embodiment of the shelf clip of the present application, and illustrate movement of the skull leg along the ratchet posts.
Figure 16B:
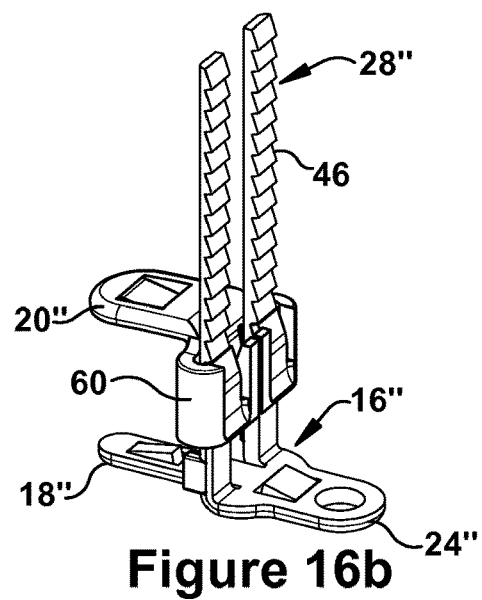
Figure 17A:
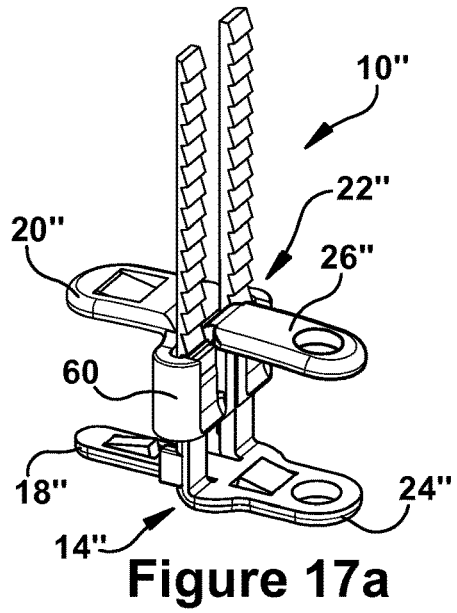
FIGS. 17a and 17b are perspective front views of the embodiment of FIG. 16, but with the leg engaged and moved along the ratchet posts.
Figure 17B:
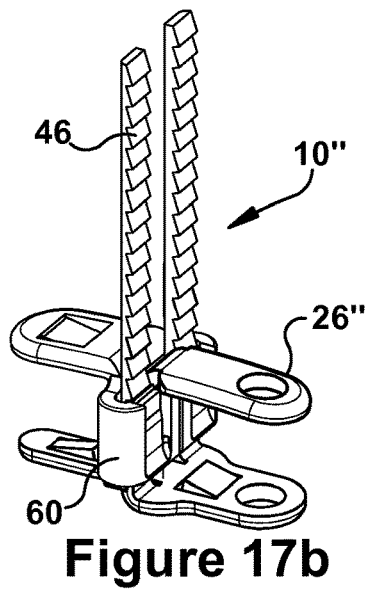
Figure 17C:
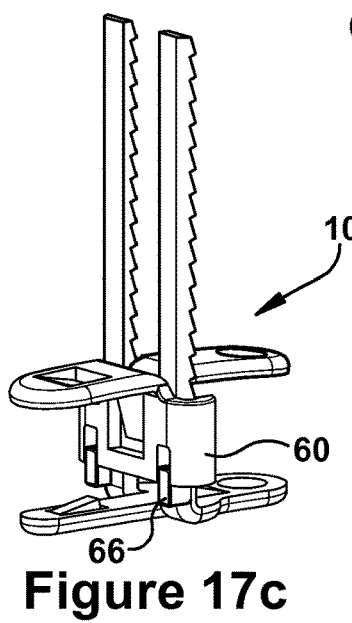
FIG. 17c is a perspective rear view of the shelf clip in FIG. 17b.

The figures depict the bone support system in various stages of implantation, and are described below. As shown in FIGS. 16a and 16b, opposing barbed legs 18", 20" extend from base 16". Locking engagement of the teeth 46" of the central post 28" with the tooth surface 62 as the ratcheting leg 20" is engaged over the angled teeth 46" to resist removal of the upper body portion 22" from the lower body portion 14". FIG. 16b illustrates movement of the ratcheting leg 20" and sleeve 60 from the position shown in FIG. 16a, toward the lower body portion 14".

Figure 18A:
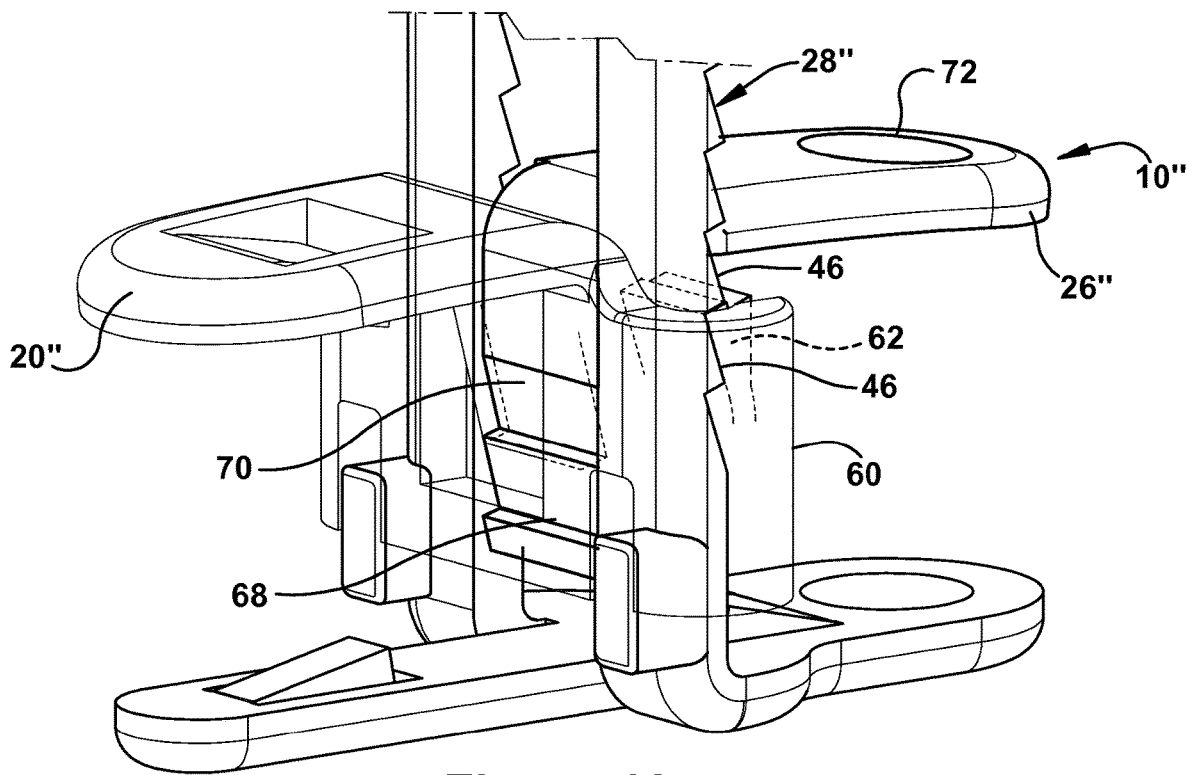
FIG. 18a is an enlarged schematic view of the shelf clip of FIG. 17c.
Figure 18B:
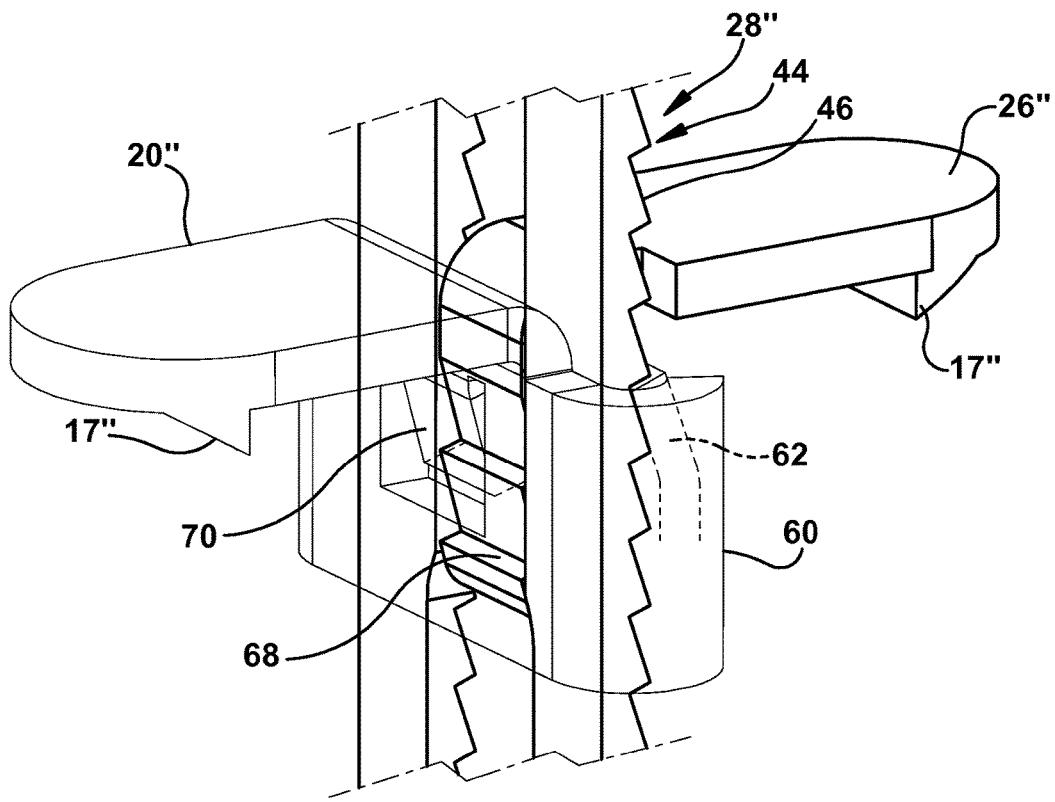

A locking leg 26" also having a locking tooth surface 68, engages with a stop surface 70 formed in the sleeve 60 of the ratcheting leg 20", resists removal of the locking leg 26" from the clip 10''', as shown in FIGS. 17a, 17b and 17c, and 23a, 23b and 23c. For optional additional strength in this embodiment, once the ratcheting leg 20" is fully engaged with the lower body portion 14", tabs 66 extending from the central post 28" are secured within mating slots 64 in sleeve 60 of the ratcheting leg. In FIGS. 18a and 18b, the locking tooth surface 68 of the locking leg 26" is shown engaged with the stop surface 70 extending out of the plane of the ratcheting leg 20". In an alternate design, teeth on the locking leg 26" could engage either the lower body portion 14" or the central post 28.

Following the convenient and secure placement of the clips, either on the skull S, or the bone flap B in another embodiment to provide a convenient reversible device which is usable on either bone edge surface, the mating bone flap or implant is then placed into the opening O in the skull S, supported on the legs 24" extending from each clip 10. In either position, the bone flap B is positioned within the opening O formed in the skull S. Where the clips 10 are secured on the edge of the skull rim, the clip serves as a support shelf 30 with the support leg 24 underneath the bone flap B, preventing it from passing into the skull cavity. The locking leg 26" is then engaged with the stop surface 70 on the sleeve 60 of ratchet leg 20 and pushed down into the sleeve of clip 10, such that the upper body portion legs ratchet downward on the ratchet surface 44" of the central post 28. This engagement enables proper height adjustment of the bone support system 12 on the skull with the bone flap. Where the clips 10 are inverted and secured on the edge of the bone flap B, the clip serves as a support ledge on the top of the bone flap, with the ratcheting leg 20 extending across the gap K to the external surface ES of the skull S to prevent the bone flap B from passing into the skull cavity. Using this inverted position, the locking leg 26 is not used, although a screw may eventually be used to secure the ratcheting leg to the bone surface. It is possible that immediately following the surgical procedure no screws would be used to allow for potential swelling and optionally re-lifting of the bone flap. Later, when desired, for example during in an outpatient procedure, the surgeon might place screws, for example through openings 72 in FIG. 14, 15 or 18a, to secure the clip 10.

To engage the locking leg 20" in position, a pointed tool or an insertion tool 75, illustrated in FIGS. 19 and 20, may be used to push down or ratchet down the teeth 68 of the locking leg 26 and ratchet leg 20 into secure position, such that the clip 10 is then engaged both on the inside surface of the skull S or bone flap B and on an external surface ES of the skull or bone flap. The insertion tool 75 has two handles 80, 81 interconnected at a hinge 82, where movement of the interconnected handles 80, 81 drives a plunger 84 to engage a locking leg of a bone support clip 10. In the illustrated embodiment, the locking leg locks into the sleeve of the ratchet leg mounted on the central post. As previously mentioned, it should be understood that in an alternate design the locking leg could also be locked into engagement with the central post. Again, the barbs 17 ensure fixation so that the clip resists removal. However, in the event conventional fixation is desired, screw holes 72 may be provided in the locking and ratchet legs 26, 20 to enable the use of screws to further secure the legs in position.

Figure 21:
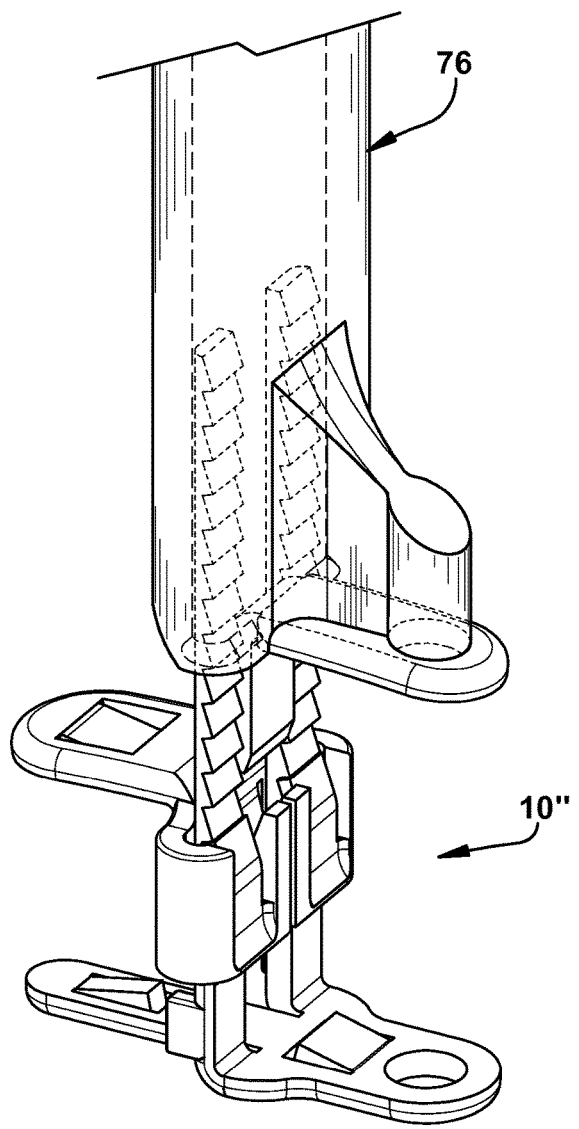
FIG. 21 is a schematic perspective view of an alternate insertion tool preparing to ratchet the locking leg of the shelf clip into engaged position.
Figure 22:
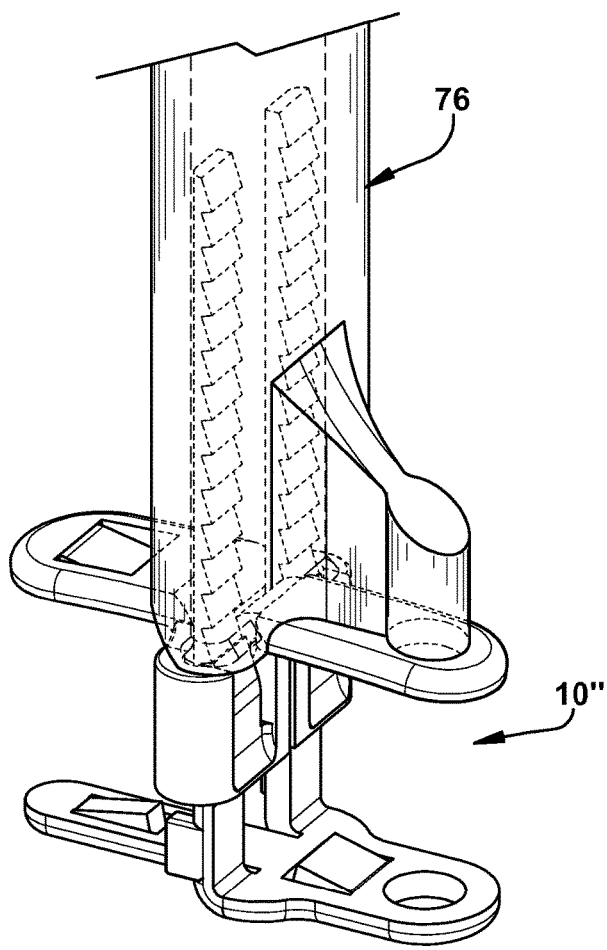
FIG. 22 is a schematic view of the tool and clip of FIG. 21 moved to a position for engagement with the bone flap.

Following locking engagement of the clip 10" with the bone flap and skull, the central post 28" of the lower body portion 14" is/are bent and/or cut to the proper height, to avoid interference once tissue T is resecured over the bone support system 12, skull S and bone flap B. In an alternate embodiment, shown in FIGS. 21a and 21b, after the bone flap B is placed on the shelf 30, a hand held tube-like member 76 is used to place the locking leg 26" and push or ratchet the locking leg into place, engaged within the bone support system 12. The hand held tube-like tool 76 is also used to break off the central post 28" that protrudes above the legs 20", 26" toward the scalp tissue T. This is accomplished by simply bending the hand held disposable tool 76 backwards once the locking leg 26" is in the desired position.

Figure 7:
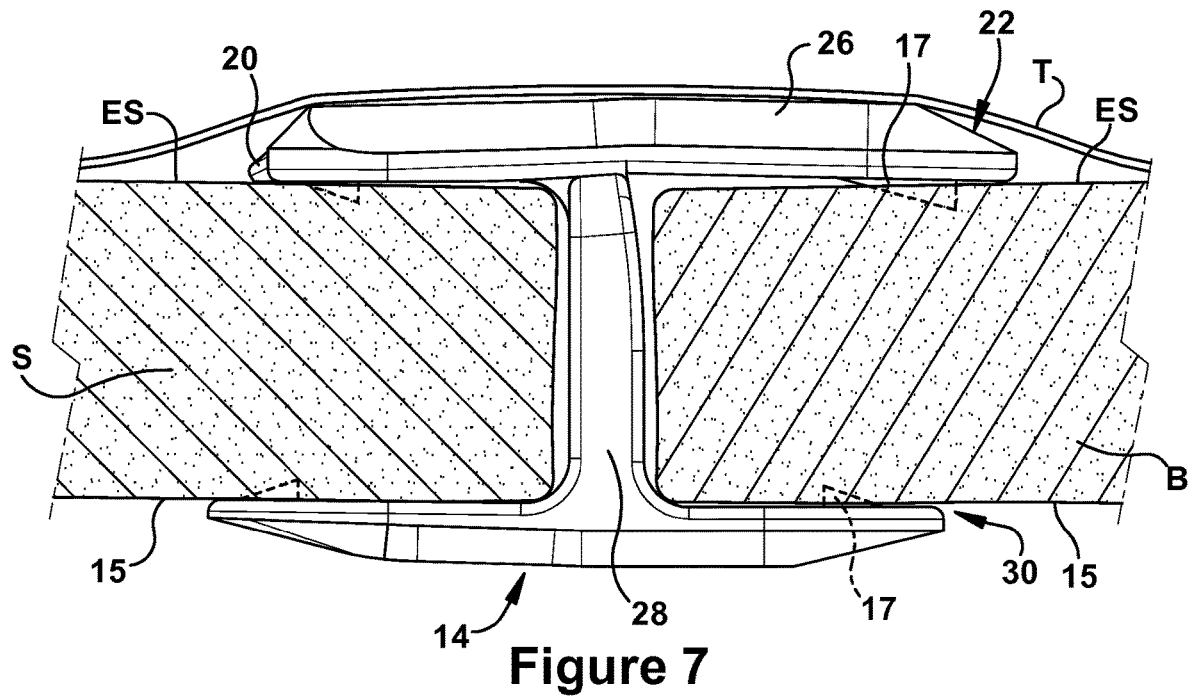
FIG. 7 is a schematic side view of the shelf clip of FIG. 6, and showing a cut-away of the skull and bone flap engaged with the shelf clip.
Figure 14:
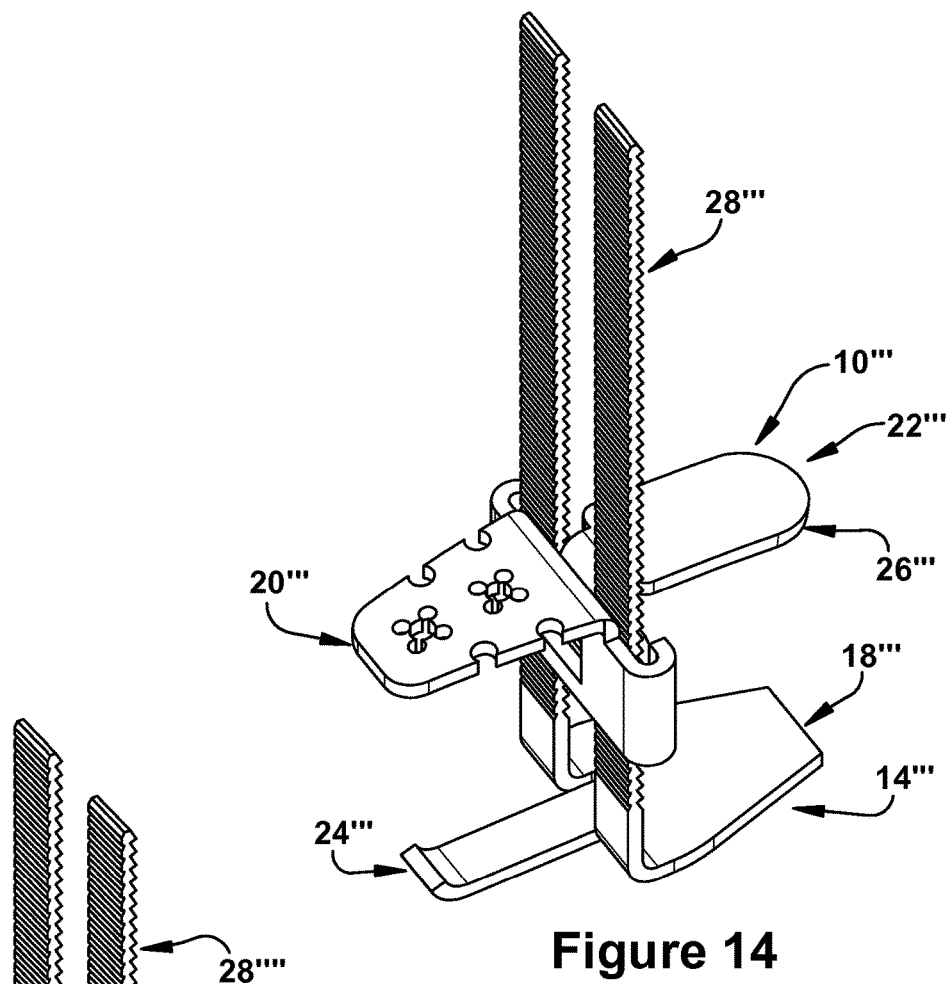
FIG. 14 is an alternate embodiment of a shelf clip of the present application, showing openings in the skull or ratcheting leg.
Figure 15:
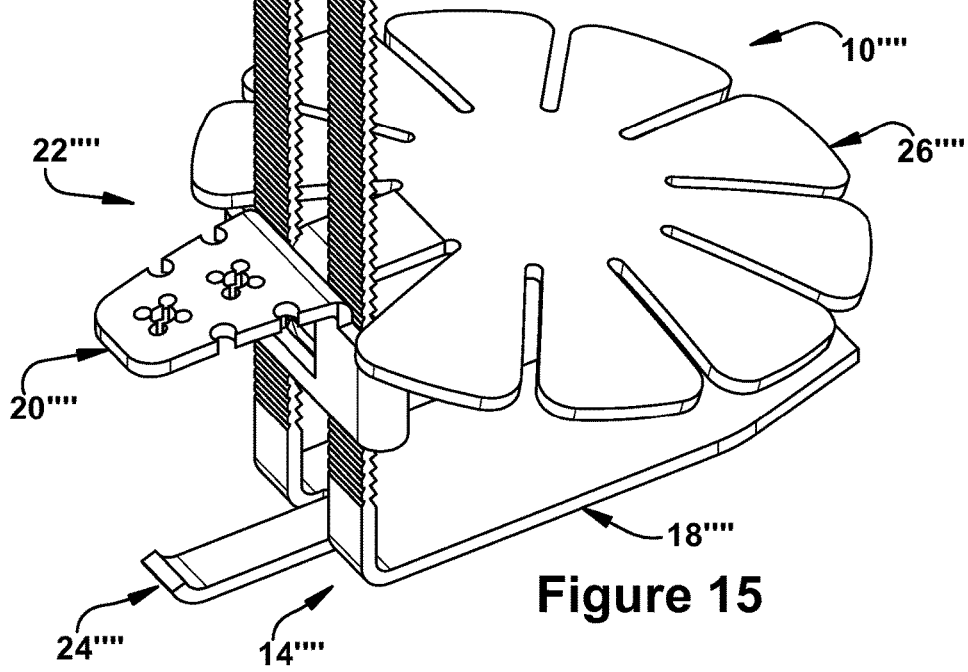
FIG. 15 is another embodiment of the shelf clip along the lines of FIG. 14, but with an alternate locking leg configuration for protecting a large skull opening, for example drill holes.
Figure 23A:
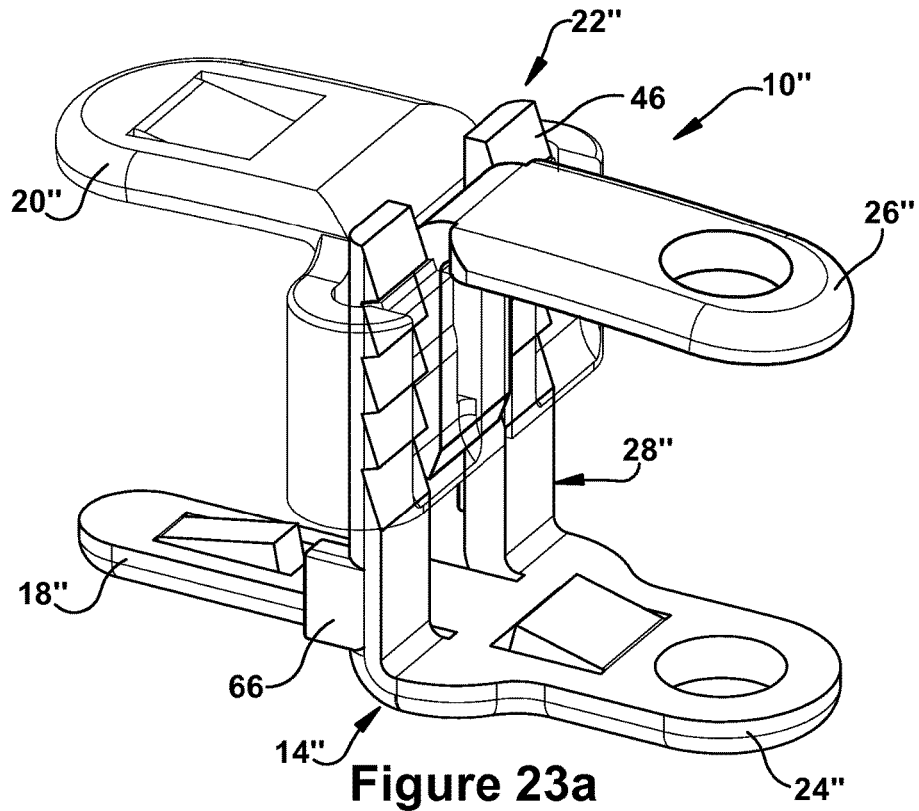
FIGS. 23a and 23b illustrate schematic front and rear perspectives of the shelf clip of FIG. 18b with the ratchet posts removed.
Figure 23B:
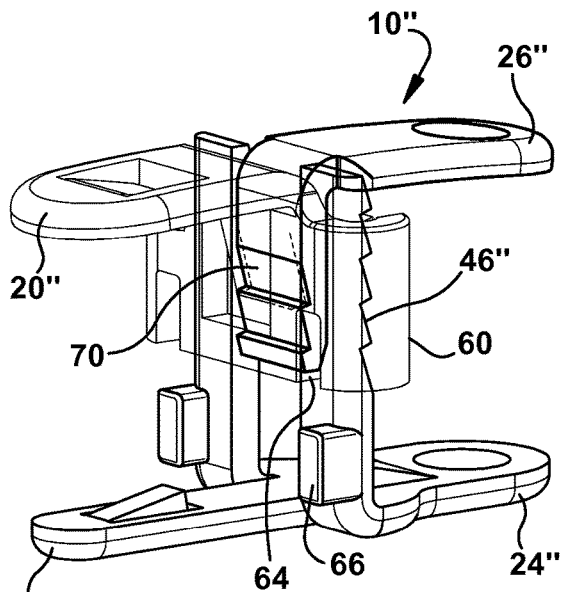
Figure 23C:
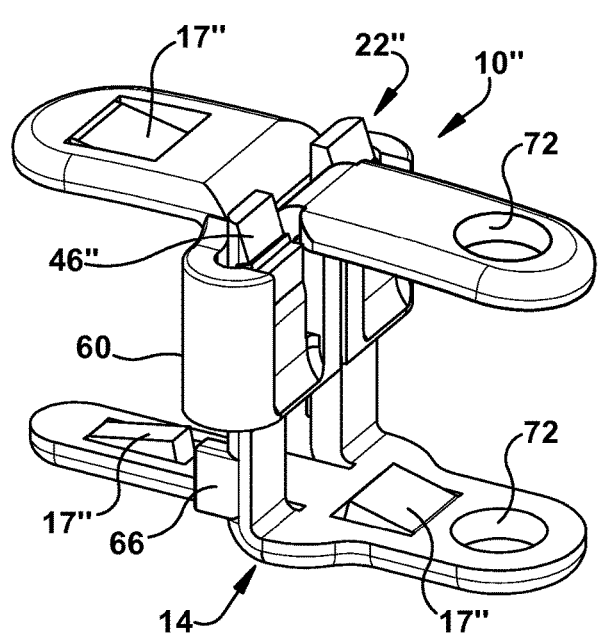

Once the central post 28" is/are trimmed to the desired profile, whether by hand or using a tool, the bone support system 12 of FIGS. 23a, 23b and 23c is secured at the desired adjusted bone thickness or height appropriate for the circumstance, surrounding bone flap or implant and skull bone along the lines schematically illustrated in FIG. 7. It should be noted that the size of the present clip device is sufficiently small that the central post which fill the gap K intermediate the bone flap B and the skull opening, are essentially similar in size to the thickness of the saw blades used to remove the bone flap, or typically 1 mm up to 3 mm in thickness. The thickness of the central post serves to substantially fill the curve or gap or kerf K and thereby carry the load in case an external force is applied which otherwise would press the bone flap into the opening.

The use of the present device to provide a fast and simple technique for easily securing the bone flap B within the skull cavity opening O provides many advantages. The shelf clip 10 device has a very low profile at the surface of the skull S and bone flap B. The height of the clip 10', 10" is adjustable for each individual situation. The shelf clip has equal or greater strength than comparable plates and screws. Reduced product inventory is required due to the adjustability of the height, and that essentially one size fits all and multiple plates and screw sizes are not required. The one size fits all ability of the present clip eliminates not only the multiple sizes and shapes of the plates and screws being replaced, but may also provide a clip device which is curved to mate with skull curvature. Less inventory generally results in less surgical preparation time due to less sterilization and less product to stock. Additionally, since one size fits all, there is less product lost during surgery in the event that an improper size is initially selected and must be discarded, as is the case with other fixation devices. Also, one size reduces the number of decisions which must be made at the end of surgery about the proper clip size.

Additional improvements making use of the embodiment of FIGS. 19 to 20 would include the use of a cartridge to be used with the insertion tool. The cartridge would be filled, for example, with multiple pre-loaded shelf clips, 4 for example, which could be easily mounted at the desired locations on the edge of the bone flap or skull cavity rim, after which the insertion tool would be used, also having the pre-loaded locking leg component of the clip for one handed pushing or ratcheting down of each locking leg into the positioned clip for ease of use. It is believed that the present shelf or ledge clip could likewise be used for temporary reconfiguration of bone fragments, for example, to reconnect bone fragments separated during a traumatic event, and requiring multiple reconnections, essentially to reform a patchwork of bone fragments either with or without implant materials or implants of PMMA, PEEK, titanium or ceramic for reconstruction into a single unit, which is otherwise a very difficult item to hold together during a surgical procedure.

We claim:
1. An implantable bone support system for closing bone openings, the implantable bone support system forming a rigid, self-supporting shelf comprising multiple rigid clips configured with at least three substantially parallel legs having a generally overall rectangular configuration, with each parallel leg extending horizontally away from a central post for engagement adjacent and surrounding the bone openings, where one upper leg extends from an upper portion of the central post and a second lower leg extends in the same direction as the upper leg but from a bottom portion of the central post, and where a third leg extends from the bottom portion of the central post in a direction away from the lower leg and is configured for extending into and below interior portions of the bone openings to locate, stabilize and retain bony structure on the rigid, self-supporting shelf within the bone opening, and thereby supports bone in-growth during the healing process to allow bone formation across the kerf/gap.

2. The system of claim 1 which is placed without the use of external fasteners, such as a screw, pin, etc.

3. The system of claim 1 which is placed without the use of any standard surgical equipment or instrumentation, such as plates, screws and screw drivers.

4. The system of claim 1 comprising clips, wherein the central post of each clip extends between an upper body portion and lower body portion, a first leg forming the upper body portion is configured to extend from the central post in a direction horizontally away from the interior portion of the bone openings, and second and third legs spaced from the first leg along the central post, each leg having a single bone engaging surface, to secure the leg in engaged position, and the second and third legs extend in opposite directions, in the same plane, and in a direction horizontally away from the central post to form the lower body portion, where the second leg is configured to extend from the central post in a direction away from the interior portion of the bone openings and the third leg is configured to extend in a direction away from the central post into the interior portion and below the bone openings and the bone engaging surface of the third leg extends to form the self-supporting shelf.

5. A support shelf or ledge positioned within and extending into skull openings comprising at least three rigid clips, each clip having at least three integrally formed barbed legs having a generally overall rectangular configuration, each of the legs extending horizontally from a central post, two of the legs configured to extend in parallel in a direction horizontally away from a top and bottom portion of the central post, respectively, and away from the skull openings, and where only one leg of the clip is configured to extend in a horizontal direction away from the bottom portion of the central post into and below the skull openings, and the clips are configured to be positioned in at least three locations surrounding the perimeter of the skull openings.

6. The clip or clips of claim 5 or 4 each comprising an additional leg or plate having a single bone engaging surface, the additional leg or plate is configured to extend from the upper body portion of the central post of the clip for providing capturing engagement surrounding the perimeter openings.

7. The system of claim 6, wherein two of the legs extend in opposite directions from a lower body portion of the clip, and one leg or plate extends from an upper body portion of the clip and wherein the upper and lower body portions of the clip are interconnected by a central post having ratchet teeth configured for engagement with the one generally rectangular leg or plate and downward ratcheting engagement of the one generally rectangular leg or plate supported on the central post into engagement with the perimeter openings and a second generally rectangular leg or plate also extending from an upper both portion of the clip extends in an opposite direction from the one generally rectangular leg or plate for downward ratcheting engagement of the second generally rectangular leg or plate supported on the central post.

8. A bone support system including a self-supporting rigid bone support clip and an insertion tool having two handles interconnected at a hinge, where movement of the interconnected handles operates only to drive a non-ratcheting plunger to engage a locking leg member of the self-supporting rigid bone support clip having three leg members, and two of the leg members of the self-supporting rigid bone support clip extend horizontally in opposite directions from a lower body portion of the clip, the third leg member extends horizontally from an upper body portion of the clip, the upper and lower body portions of the clip are interconnected by a central post having ratchet teeth for engagement with the third leg member for downward ratcheting engagement of the third leg member supported on the central post, and the locking leg member is driven by the non-ratcheting plunger of the tool into downward ratcheting engagement of the locking leg member on the central post.

* * * * *